United States Patent
Carmichael et al.

(10) Patent No.: US 8,784,747 B2
(45) Date of Patent: Jul. 22, 2014

(54) FRAGRANCE DISPENSER FOR USE WITH PORTABLE ELECTRONIC DEVICE

(71) Applicants: Marcy Carmichael, Radcliff, KY (US); Constance Blake, Louisville, KY (US)

(72) Inventors: Marcy Carmichael, Radcliff, KY (US); Constance Blake, Louisville, KY (US)

(*) Notice: Subject to any disclaimer, the term of this patent is extended or adjusted under 35 U.S.C. 154(b) by 0 days.

(21) Appl. No.: 13/694,710

(22) Filed: Dec. 26, 2012

(65) Prior Publication Data

US 2013/0164178 A1    Jun. 27, 2013

Related U.S. Application Data

(60) Provisional application No. 61/630,956, filed on Dec. 22, 2011.

(51) Int. Cl.
*A61L 9/00* (2006.01)
*A24F 25/00* (2006.01)
*B01D 47/00* (2006.01)

(52) U.S. Cl.
USPC ............................. 422/306; 239/34; 261/75

(58) Field of Classification Search
USPC ................ 422/5, 125, 306; 239/34; 261/75
See application file for complete search history.

(56) References Cited

U.S. PATENT DOCUMENTS

| | | | |
|---|---|---|---|
| 6,938,832 B2 | 9/2005 | Sada | |
| 7,152,758 B2 | 12/2006 | Fazzio | |
| 7,160,515 B2 * | 1/2007 | Murdell et al. | 422/123 |
| 7,512,415 B2 | 3/2009 | Fazzio | |
| 7,622,073 B2 * | 11/2009 | Schramm et al. | 422/5 |
| 2004/0203412 A1 | 10/2004 | Greco | |
| 2004/0204043 A1 | 10/2004 | Wang | |
| 2004/0235430 A1 | 11/2004 | Ma et al. | |
| 2006/0293871 A1 | 12/2006 | Fazzio | |
| 2007/0098148 A1 | 5/2007 | Sherman | |
| 2008/0070567 A1 | 3/2008 | Sadler | |
| 2008/0295457 A1 | 12/2008 | Kaniecki | |
| 2008/0313789 A1 | 12/2008 | Manne | |
| 2009/0261181 A1 | 10/2009 | Cheung | |
| 2010/0140371 A1 | 6/2010 | Zuo | |

* cited by examiner

*Primary Examiner* — Monzer R Chorbaji
(74) *Attorney, Agent, or Firm* — Carrithers Law Office, PLLC

(57) ABSTRACT

A cover for holding and protecting a scent insert for use with a portable electronic device or other electronic device such as an IPOD, IPAD, MP3 player, laptop, for example, including a pocket for holding a removable scented insert. The pocket is an integral part of the cover or a removable pocket which is held on to the outside of the cover with an adhesive, for example. The aromatic insert is a scent impregnated porous plastic insert or plastic insert having a permeable layer sealed with nonpermeable peelable layers of plastic or paper film wherein a top layer is removed as desired, thus releasing the desired aroma. The exterior surface of the pocket is porous or includes apertures or slits for transferring the scent outside of the pocket insert holder.

16 Claims, 2 Drawing Sheets

FRAGRANCE DISPENSER FOR USE WITH PORTABLE ELECTRONIC DEVICE

CROSS REFERENCES TO RELATED APPLICATIONS

This application claims priority from Provisional Application Ser. No. 61/630,956 filed on Dec. 22, 2011 which is incorporated by reference herein.

TECHNICAL FIELD

The present invention relates to the field of scent delivery devices used in conjunction with hand held electronic devices such as cell phones, tablets, IPOD, MP3 players, laptops, thus enabling a user to enjoy an aroma emitted from a removable and replaceable scent insert disposed in a pocket of holding means secured to the device having a fragrance detectable o the user when the device is used or when the device is in close proximity to the user.

BACKGROUND OF THE INVENTION

Aroma emitting devices are well known and are commonly used in homes and commercial establishments to provide a pleasant atmosphere for people in given areas. Such devices passively or actively transmit aromas to the general surroundings. Examples of passive devices include air wicks, scented gel-packs, and aromatic sticks resting in a bottle of aromatic liquid and protruding out of the bottle so that the liquid is absorbed and drawn upward through the stick where upon, the liquid evaporates from the surface of the stick. One type of active aromatic device is plugged into an electrical power outlet, whereupon, a small heating element heats an aromatic liquid containing member thus causing the liquid to evaporate and escape into the adjacent surroundings. Another example of an active aromatic device is powered by battery or wall outlet and sprays an aromatic mist periodically into a room.

Aromatic devices are commonly used by individuals who enjoy various selected scents. Further, the use of such aromatic devices has been found to improve or enhance the general demeanor of individuals in a particular surroundings. Certain scents have been found to cause desirable mood changes in people in general.

Users of portable electronic devices, portable music players and gaming units such as pads, IPOD, MP3 players and laptops are often on the move or are not in an area where scent emitting devices are present. A combination including aroma delivery devices and electronic entertainment or communication devices allows a user to enjoy the use of the device while enjoying a pleasant aroma at the same time.

DESCRIPTION OF THE RELATED ART

US Patent Application Publication No. 20070098148 for AROMA RELEASING PATCH ON MOBILE TELEPHONES by Sherman published on May 3, 2007 teaches an aromatic patch held onto the surface of a portable electronic device by an adhesive. There is no mention of an easily replaceable aromatic insert or a pocket within which to place the insert.

US Patent Application Publication No. 20040235430 for MOBILE PHONE AND SCENT DISPENSER THEREOF by Ma et al published on Nov. 25, 2004 teaches a portable electronic device with an aromatic liquid stored in tank in communication with a dispersal device such as an electrically powered thermal resistance heater, unlike the present invention which is passive and does not rely on a powered dispersing of the scent.

U.S. Pat. No. 6,938,832 for SCENT STRIP by SAA which issued on Sep. 6, 2005 teaches a multilayered package of aromatic strips adhered to the case of a CD, DVD or V.S. tape. The user peals off the top layer of the stack, one at a time, to release a scent. There is no mention of the use of a peelable stack of aromatic layers in combination with a music player, gaming device or a communication device such as a cell phone.

US Patent Application Publication No. 20080313789 for PORTABLE SCENT DELIVERY DEVICE by Manned which issued on Dec. 25, 2008, teaches a portable scent delivery system which can be used in conjunction with electronic devices such as a PDA, DVD player, gaming devices, for example. Manned's scent delivery systems rely on motor driven belts or electrically powered thermal units to deliver the scent unlike the present invention which used passive evaporation of aromatic volatiles to deliver the aroma.

U.S. Pat. No. 6,309,715 sets forth several patents which describe methods of incorporating a slow sustained release of a fragrant molecule as follows: U.S. Pat. Nos. 5,525,588; 5,525,555; 5,490,982; 5,372,806 describe dissolving or suspending fragrance compounds in emulsions. U.S. Pat. Nos. 5,500,223; 5,324,444; 5,185,155; 5,176,903; and 5,130,171 describe encapsulation of a flagrance. U.S. Pat. No. 5,234,689 describes dissolving a fragrance into a hydrophilic phase such as silicone; U.S. Pat. Nos. 5,387,622 and 5,387,411 incorporation of a fragrance into a cross-liked polymer. U.S. Pat. Nos. 5,071,704 and 5,008,115 incorporate a fragrance into a permanent laminate. U.S. Pat. No. 4,908,208 incorporate a fragrance that softens at body temperature. U.S. Pat. Nos. 4,524, 018 and 4,500,725 describe incorporation of a fragrance into silanes with fragrant alcohol to form alkoxysilanes. U.S. Pat. No. 6,054,547 describes the incorporation of fragrant moieties via hydrosilation of an olefinic silane molecule. U.S. Pat. No. 5,034,222 describes a solid composite air freshening article in a granular foam phase dispersed throughout a gelled phase. U.S. Pat. No. 6,063,365 describes an emulsifier-free nonporous, continuous permeable polymeric film having an entrapped and dissolved fragrance capable of evolving from the film into the environment by means of molecular diffusion in a sustained and controlled release manner. The disclosure of the above U.S. patents are hereby incorporated by reference herein as if set forth in their entirety.

SUMMARY OF THE INVENTION

In accordance with the present invention, there is provided a device for securing a removable fragrance insert to the panel or protective cover of a portable electronic mobile device. The scented insert is capable of releasing fragrant vapors in the surrounding air. In one preferred embodiment a recess or cavity having a selected shape and size is formed on or within the inner or outer panel of a portable electronic device, in the inner or outer panel of a protective or decorative cover of a portable electronic device, or therebetween. A fragrance substrate or element or corresponding size and shape is inserted and removably held in position by frictional force or a tacky composition providing means for removal and replacement of the fragrance element. In another preferred embodiment, a thin sheet, strip or ribbon of flexible elastomeric, plastic, rubber, cellular foam type material having an adhesive covering one side protected by a peelable film can be formed such as by molding or pressing or punching with a depression, cavity, or recess of a selected size and shape and adhered to a surface of a mobile device, a surface of a protective or decorative cover of a mobile device or disposed therebetween. Insertable fragrant substrates having a corresponding size and shape can be disposed within the cavities or recess providing a flush smooth fit. Furthermore, use of an elastomeric or cellular form compound provides a pliable holder which need not interfere with the use of a protective cover over the mobile device if so desired. In another embodiment, the insert is held within the pocket by a door configured to rotate on a hinge. The hinge is integral with the door and the portable electronic device cover.

The air freshener or fragrance insert consists of a substrate impregnated with a substance that is time released into the surrounding air and in which such substance, when in the air, can, upon appropriate choice, provide a pleasant aroma.

It is a further object of the present invention to provide a disposable fragrance insert means wherein a particular scent or aroma can be detected by the user and limited in distribution to be detectable by the individual user of a hand held device and provide a means for aroma therapy with selected scents including fruit and berry scents, such as evergreen scents, citrus scents, vanilla, and spice scents.

It is a further object of the present invention to provide a disposable and replaceable fragrance insert element disposed or contained within an adapter such as a bracket or pocket wherein the fragrance substance is comprised of one or more of solid particles, beads, platelets, discs, strips, or bars, impregnated with a substance that is time released into the surrounding air and in which such substance when in the air can upon appropriate choice provide a pleasant aroma.

It is an object of this invention to provide a combination comprising an entertainment or communication device combined with a scent delivery system which is passive in nature, that is, the scent delivery system is not a powered system but only relies on evaporation of scented volatile.

It is an object of this invention to provide a combination comprising an entertainment or communication device combined with a scent delivery system wherein a separate cover is provided for the entertainment or communication device and wherein the cover includes a pocket which removably holds a replaceable aromatic insert.

It is an object of this invention to provide a combination comprising an entertainment or communication device combined with a scent delivery system wherein a separate cover is provided for the entertainment or communication device and wherein the pocket which removably holds a replaceable aromatic insert is contains pores, apertures or slits which enhance the evaporation of the aromatic volatile contained in an aromatic insert.

It is an object of this invention to provide a combination comprising an entertainment or communication device combined with a scent delivery system wherein a pocket or sleeve is attached to an otherwise unused area on the surface of the device and wherein the pocket removably holds a replaceable aromatic insert.

It is an object of this invention to provide a combination comprising an entertainment or communication device combined with a scent delivery system wherein a replaceable aromatic insert is used and wherein the insert includes copolymer ethylene vinyl acetate (or EVA) as a substrate or carrier for the aromatic volatiles.

Other objects, features, and advantages of the invention will be apparent with the following detailed description taken in conjunction with the accompanying drawings showing a preferred embodiment of the invention.

BRIEF DESCRIPTION OF THE DRAWINGS

A better understanding of the present invention will be had upon reference to the following description in conjunction with the accompanying drawings in which like numerals refer to like parts throughout the views wherein.

DESCRIPTION OF THE PREFERRED EMBODIMENTS

Figure 1:
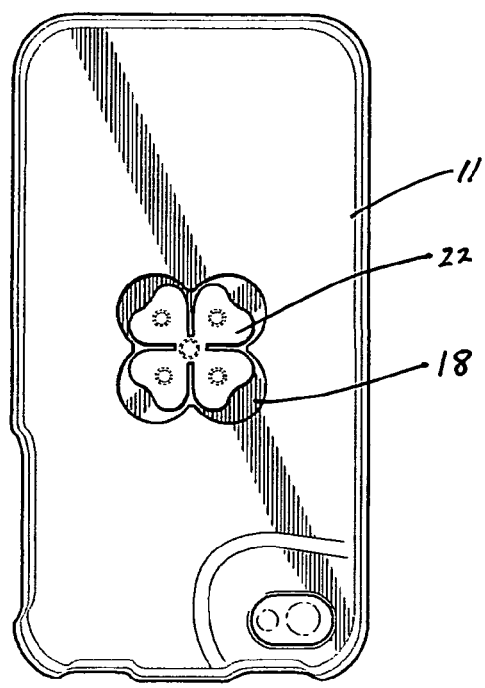
FIG. 1 is a rear perspective view of the scented insert inside the pocket on the rear side of a portable electronic device cover.

The air freshener and fragrant emitting substance of the present invention consist essentially of a substrate impregnated with a substance that is time released into the surrounding air and in which such substance when in the air can upon appropriate choice provide a pleasant aroma.

The scent emitter maybe variously formed, shaped and/or in various sizes and formulated and designed for consistency in the release of a scent over a long period of time and in this regard a long period of time is considered by applicant to be up to at least 45 days. The particular form of the air freshener unit and/or form, shape or size of the scent emitting material is not an essential part of the present invention other than having the scent emitter physically in a solid state and most preferably in the form of beads, pellets, flat disc, pills or films which maybe either uniform or non-uniform in size and preferably with the scent release being consistent over a long period of time.

A particular scent or aroma can provide a means for aroma therapy with selected scents and fragrances. The fragrance oil can be any natural substance, synthetic material, (incorporating aldehydes, ketones, esters, and other chemical constituents), or combinations thereof which is known in the art and suitable for use in candles for imparting an odor, aroma, or fragrance. Suitable natural and synthetic fragrance/flavor substances include those compiled by the U.S. Food and Drug Administration in Title 21 of the Code of Federal Regulations, Sections 172.510 and 172.515 respectively. Suitable fragrances include spice oil, flower oil, and fruit oil. The fragrance oil may contain fragrance components, for example benzaldehydes, phenols, cinnamic aldehydes and esters, octadienes, dienes, cyclohexadienes, and terpenes.

The fragrances may comprise an essential oil in a carrier such as water and/or alcohol or other organic solvent or even a perfume. The fragrance may be that of a fruit and berry scents such as: citrus, almond, apple, cherry, grape, pear, pineapple, orange, strawberry, raspberry, and musk; flower scents such as lavender, rose, iris, carnation, gardenia, tea rose, violet, hyacinth, magnolia, mimosa, honeysuckle, jasmine, narcissus, orange blossom, orchids, sweet pea, tuberose, and lilac; forest and herbal smells such as evergreen cedar, pine, sassafras, and spruce; essential oils such as spice, peppermint, vanilla, spearmint; and various other fragrances such as leather, new car odor, acacia, cassie, cypre, cyclamen, fern, hawthorn and the like. The fragrance is not critical so long as it is compatible with the polymer impregnated with the time release carrier. The level of fragrance can vary up to about 100 percent by weight and more preferably from 0.001 to about 100 percent by weight. Other agents such as surfactants, emulsifiers, and polymers can be used to encapsulate the fragrance. Moreover, pellets, beads, discs or other fragrant substrates can be molded or formed from fragrance impregnated wax providing a scent releasing substrate.

The carrier and means of controlling the release of the selected fragrance is dependent upon many variables including time and temperature with respect to the environment inside and outside of the vehicle. The fragrance and substrate composition comprising of 0.5% to 99.5% by weight of a suitable substrate and from 0.5% to 90% by weight of a fragrance oil.

It is also contemplated that the scented material may be composed of 100 percent of the fragrant raw material without a solvent or essential oil. Furthermore, the fragrance can be imparted to the fragrance compound absorbent material as an aerosol or gas vapor separate from, or in combination with a liquid substrate.

In one preferred embodiment, the fragrance can be absorbed by a polymeric material such as an ethyl vinyl acetate polymer simply by being disposed in close proximity thereto. Ethyl vinyl alcohol resin is another polymer having good scent absorbent capabilities which can be formed in pellets, beads, discs, buttons, bars, or molded into fanciful shapes and may include elastomeric properties enabling the molded fragrance emitting compounds to be pressed into cavities formed in a holding means such as a pocket attached to a selected surface of a hand held device.

One preferred group of copolymers of ethylene and vinyl acetate which absorb odors are produced by DuPont Industrial Polymers under the trade name of ELVAX resins which generally range in vinyl acetate content from 9 to 40% and have melt indexes from 0.3 to 500 dg/min. Moreover, the ELVAX resin from DuPont does not incorporate a plasticizer which could interfere with the scent absorbing capability of the polymer. The polymer can be formed in any desired shape prior to treatment or under low heat conditions (70° C. or less). The ELVAX resin can be extruded or molded and blended with polyethylene, polypropylene, ABS resins, thermoplastic rubber nitril rubbers, natural rubber and other elastomers.

The amount of scent adsorbed into the vinyl acetate substrate and the control release mechanism is dependent upon the time and temperature relationship between the scent and substrate as well as the volatility of the scent, content or density of the polymer, level of polymerization, surface area (porosity), and pore size and structure of the polymer substrate which in the instant example is a vinyl acetate absorbent material. Thus, the impregnation occurs through passive adsorption and the time release mechanism occurs through passive diffusion.

As described in U.S. Pat. No. 2,169,055 by Overshiner et al., a cellulose compound such as cellulose acetate or cellulose nitrate can be imparted with a compatible scent imparting material which is released over an extended period of time. The cellulose compound can be produced in a solution with an organic solvent such as acetone and 1,4 diethylene oxide, and adding a scent imparting essential oil to the solution. Plasticizers such as diethyl phthalate and tri-acetic acid ester of glycerin may be used to impart flexibility to the material. The solution may be formed in to sheets, pellets, drops, discs, bars, films or the like by casting or molding. The solvents evaporate and a porous cellular structure is formed which releases the essential oil at a rate to provide an odor lasting for several months. Moreover, the scent impregnated polymer can be over wrapped and crimped at desired intervals in air tight and inpermerable paper, plastic film, or metal foil to form an air tight seal utilizing a nonpermeable vacuum sealed material to prevent premature release of the scent in storage or packaging. Thus, the product can be air evacuated, or even vacuum sealed, in order to prevent release of the scent from the polymeric substrate prior to installation. The strength of the scent may also be determined by the quantity or size of the individual polymer units, (beads, disc, bars or particle containing pockets), which are cut from the roll and insertable into a holding pocket. Thus, the customer can decide upon the strength of the air freshener filter insert by using multiple packs, beads, or layers of strips or film sheets. The utilization of sealed polymer substrates containing scents provides a method of prolonging and maintaining the shelf life and consistency of the time release product.

Micro encapsulation provides a method of controlling the release of scent in liquid form by enclosing the scent within hollow shells of differing size and wall thickness which can be dissolved or ruptured at different intervals to provide a generally steady supply of scent exposed to the environment. Moreover, semipermeable shells which allow escape through the shell wall without shell rupture exist to control the release of a scent.

Another method of controlling the release of the scent from a carrier is to use a homogeneous semipermeable material containing the active ingredient as a pure impregnate, solute or precipitate. The semipermeable material serves as the carrier from which it can only slowly escape by solution, diffusion, evaporation or combinations thereof. The characteristics of the carrier material depends on properties such as pore size, compatibility with the environment, liquid content, temperature of environment, wet-ability, and processing parameters.

One type of polymer liquid composite material prepared which can be utilized in the present invention is an organic or inorganic cellulose ester such as cellulose triacetate or cellulose nitrate as vehicles for the controlled release of active materials into the environment. As described in U.S. Pat. No. 3,985,298 by Nichols and incorporated by reference herein, the composite material can be formed to prepare transparent coherent materials formed as films, fibers or microspheres. The scent may be carried in a fluid which may comprise water, alcohol, ether, aliphatic and aromatic hydrocarbons, ketones, esters, and combinations thereof together with other chemical constituents. For instance, the chemical composition comprising the selected fragrance or scent may be incorporated as a component in an aerosol propellant, gas, or liquid containing a solvent carrier such as water and/or alcohol together with an essential oil having a selected fragrance or perfume for impregnation into the polymer-liquid composite. These polymer-liquid composite materials are prepared to incorporate interconnected internal pores from about 1 to 500 microns. These polymer-liquid composites often possess oleophilic hydrophobic surfaces and can contain release retarding gums and oils from which hydrophilic and oleophobic vehicles can be expelled by surface forces. Moreover, active ingredients can be incorporated in polymer-liquid composites as soluble particles or precipitates formed by solvent exchange or chemical reaction in situ to provide an internal reservoir which maintains a constant concentration of the active ingredient in solution inside the polymer-liquid composite. Thus, the polymer-liquid composite provides a means for zero-order release in which a nearly uniform level of active ingredient (scent) is maintained throughout the active life of the vehicle. The polymer-liquid composite material provides a means of retarding the evaporative release of volatile materials though diffusive effects and control of effective surface area, as well as through depression in the vapor pressure of the volatile substance. Furthermore, the polymer-liquid composite can be modified by skinning, by coating with a liquid to impede escape of the active ingredient (scent) or by the addition of a release-promoting agent to the environment.

In accordance with the present invention as shown in FIG. 1-4, there is provided a fragrance substrate of porous material insertable into one or more envelopes or pockets attached to the exterior surface of a hand held device such as a portable electronic device or tablet. The pocket holds captive therein a selected quantity of a scented particulate material. The pockets are preferably made of a mesh, film or other polymeric material allowing for air to flow readily therefrom. For example, the mesh may be fabricated from paper, cloth, synthetic material and combinations thereof such as fiberglass, nylon, polyester, polyethylene or the like. Moreover, a fibrous material, film or molded aromatic material including openings therein may also be substituted for the mesh. The scented particulate material comprising the fragrant element is composed of beads, discs, of film strips or molded porous or scent impregnated polymer such as an acetate material impregnated with a substance having a preselected scent may be suitable. The porosity of the material is obviously co-related to the particle size of the particulate material so as to retain the particulate material. The pockets may have a top surface and bottom surface wherein the bottom surface adheres to the surface of the hand held device with the top surface or layer of material is air permeable and covers the fragrance substrate disposed therein. The top surface may include a layer of air impermeable material such as a film or foil which may be removably attached to a selected portion of the bottom sheet of the pocket to provide an air tight seal with locking ribs, a zipper lock, or folding flap means. An air permeable flap could also be combined with adhesive substances along an edge to form an air tight seal which could repeatably opened and sealed by the user.

Figure 2:
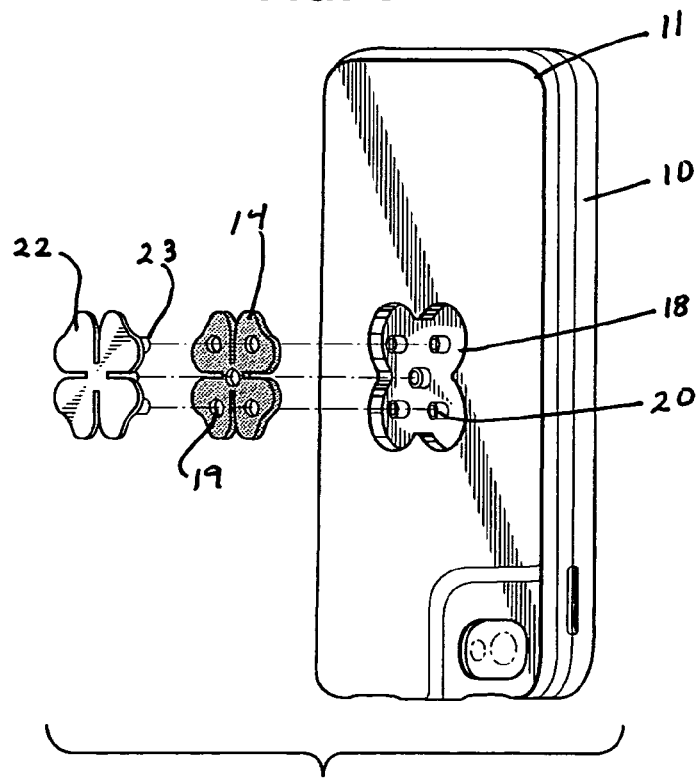
FIG. 2 is a rear view of a portable electronic device showing a molding or cavity formed in the back panel surface of a portable electronic device or its protective cover providing a cavity or recess therein and a fragrance substrate or element disposed therein with a cover thereover providing a smooth fit and flush surface.

The embodiment shown in FIGS. 1-2 shows a portable electronic device 10 cover 11 including a recess or pocket or envelope 18 specifically configured to removably hold a scented insert element 14 which allows a fragrance impregnated within a polymer and disposed within the scented insert 14 to evaporate into the air for the purpose of improving the perceived aroma in close proximity to the user.

The scented insert 14 is held in the pocket 18 by a cover 16 which is of a fanciful ornamental design. The scented insert may be of the same ornamental design as the cover or sized to fit within the cavity 18. The preferred embodiment shown in FIGS. 1-2 utilizes a cover with the cavity formed having a particular shape "a clover leaf" and orienting means 20 comprising at least one and preferably a plurality of pegs which cooperatively engage slots, holes or other orienting means 19 such as apertures formed in the substrate 14. The inner surface of the clover shaped cover 22 includes cooperatively engaging holding means such as studs or apertures which align with the substrate 14 and cavity 18 to hold the substrate in position by a friction fit, adhesive or other means for securing the cover within the cavity to provide a flush fit and smooth surface on the back of the electronic device cover.

Scented insert 14 is formed from a material which can absorb a selected fragrance. It is anticipated that the insert includes copolymer ethylene vinyl acetate (or EVA) as a substrate or carrier for the aromatic volatiles.

Figure 3:
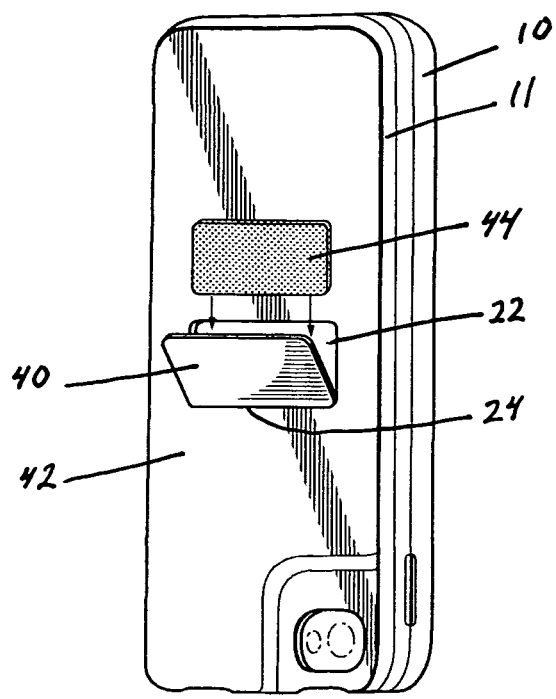
FIG. 3 is a rear perspective view of the scented insert being placed into the pocket on the rear side of a portable electronic device cover.

As best illustrated in FIG. 3, the pockets can be separately formed and suitably attached to the base surface a suitable adhesive or fusion bonding using heat and/or suitable solvents or formed by cutting a flap 40 from a layer of the cover 42 or attachment of a flap 40 to the cover by welding, by an adhesive or by integrally forming the flap from the cover upon fabrication of the cover. The pocket or envelope may be filled with a selected quantity of fragrance impregnated substrates 44 (beads) acetate beads, scented polymer or foam or the equivalent. Moreover, flakes, strips of material, or solid bars may be used to form bars, strips, or wedges which may be disposed within the pockets and held within the envelope or molded and formed or disposed in slits or depressions formed therein. The flap may be adhesively retained by an adhesive having releasable and reusable properties, a friction fit, hook and loop fasteners or other suitable holding means known in the art.

The scented insert 44 is held in the pocket 22 by the door 40 which swings on a hinge 24 from the cell phone 10 cover 11. Hinge 24 is preferably a 'living hinge' which is made integrally with the door 40 and the portable electronic device cover 10, as part of the injection molding process. Preferably, door 40 is held closed by friction at the adjacent edges of the pocket 22. The door 40 may include a tab which establishes an interference fit with the adjacent edge of portable electronic device cover 10.

Figure 4:
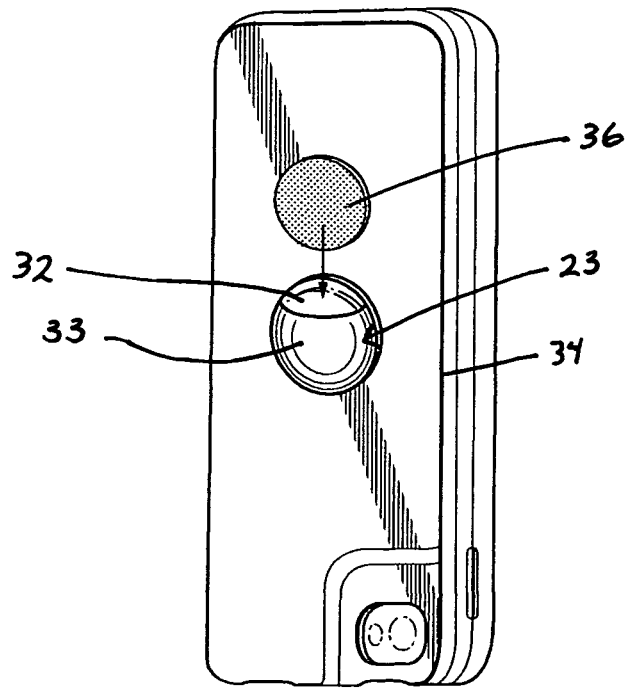
FIG. 4 is a rear perspective view of a scented insert being placed into a pocket for holding a scented insert on the rear side of a portable electronic device.

Another preferred embodiment of the present invention shown in FIG. 4, is a pocket 23 configured to hold a scented insert. The pocket includes a front panel 33, a back panel 32. Pocket 23 is preferably held onto rear side of a portable electronic device with adhesive which is included on the rear surface of back panel 34.

Pocket 23 includes an opening through which a scented insert 36 is placed within pocket 23, as shown in FIG. 4. It can be seen that the gap between front wall 33 and back wall 32 is large enough to allow the scented insert 36 to be slipped into the pocket 23. Furthermore, the pocket 23 can be formed as a bubble having slit therein forming a top cover and bottom pocket which cooperatively fit together to provide a closed bubble. The pocket cover may includes slits or openings. The scent held within insert 36 evaporates and escapes out through slits and openings and on out into the desired surroundings where a user resides.

It is anticipated that a base comprising a polymer or elastomer can be molded presenting a virtually flat profile adhesively attached to a surface of the user's device, whereby a depression or shallow cavity can be formed therein. Moreover, the cavity and insert can be molded into corresponding fanciful shapes such as hearts, discs, logos, letters, trademarks, designs, mascots, etc.

The fragrant elements are molded or otherwise formed of a scented material and typically comprises a porous material such as an acetate polymer impregnated with a scent. The freshener element may be enclosed in a porous means for holding such as a pocket or the like. It is also contemplated that the fragrant element may be formed of a soft pliable material such a highly plasticized polymer or material held in pockets or other means of retaining forming a frame in order to provide a means for inter nesting the fragrant elements in the cavity or depression of an adapter or other means of holding formed integrally into or adhered to a surface. The fragrant material can be affixed to a support backing of permeable material such as a web, frame or other permeable material such as a sheet of plastic having openings there through by molding, gluing, or impregnation by melting thereto. An important consideration is to provide as much surface area as possible to maximize the exposure of the air to the air freshener filter insert element.

For instance, the slim profile of the adapter or pocket can be an adherable molding which is removably secured to the surface of the telephone, such as the back, wherein a fragrant insert or element is disposed in a cavity of the molding presenting a smooth flat surface which could be covered by a protective cover such as a hard shell cover or elastomer cover which fits over the back of a cell phone, I-POD or the like. The insert would fit in the cavity like a puzzle piece and could have any type of corresponding peripheral profile.

The scented insert is capable of releasing fragrant vapors in the surrounding air. In one preferred embodiment a recess or cavity having a selected shape and size is formed on or within the inner or outer panel of a portable electronic device, in the inner or outer panel of a protective or decorative cover of a portable electronic device, or therebetween. A fragrance substrate or element or corresponding size and shape is inserted and removably held in position by frictional force or a tacky composition providing means for removal and replacement of the fragrance element.

It is contemplated that the fragrance element can comprise a porous film or thin strip of material having openings therein sandwiched between two layers of gas impermeable material consisting of a base strip and cover strip or film comprising a mesh or other air permeable support material such as a plastic grid, perforated paper, plastic, or fabric. Optionally, a thin layer of a weak adhesive can can be disposed on a selected surface of the support material and covered with a removable and/or peelable film or paper backing. The adhesive can serve to affix the fragrance element or strip. The adhesive may also be applied to one side of the removable film or paper and applied to the roll of fragrant strip during the fabrication of same.

For instance, in one preferred embodiment, a thin sheet, strip or ribbon of flexible elastomeric, plastic, rubber, cellular foam type material having an adhesive covering one side protected by a peelable film can be formed such as by molding or pressing or punching with a depression, cavity, or recess of a selected size and shape and adhered to a surface of a mobile device, a surface of a protective or decorative cover of a mobile device or disposed therebetween. Insertable fragrant substrates having a corresponding size and shape can be disposed within the cavities or recess providing a flush smooth fit. Furthermore, use of an elastomeric or cellular form compound provides a pliable holder which need not interfere with the use of a protective cover over the mobile device if so desired.

While the above embodiments are described for use with portable electronic devices, it is to be understood that covers with pockets for holding scent inserts or stand alone pockets for holding scented inserts are equally applicable to portable music players and gaming units such as tablets, IPOD, MP3 players and laptops or other such consumer electronic personal use devices.

The foregoing detailed description is given primarily for clearness of understanding and no unnecessary limitations are to be understood therefrom, for modification will become obvious to those skilled in the art upon reading this disclosure and may be made upon departing from the spirit of the invention and scope of the appended claims. Accordingly, this invention is not intended to be limited by the specific exemplification presented herein above. Rather, what is intended to be covered is within the spirit and scope of the appended claims.

We claim:

1. A fragrance dispenser case for a portable electronic device consisting of:
   a protective case having a front panel connecting to a back panel by opposing corresponding connecting side edges in parallel with one another in a spaced apart relationship for removably covering a portable electronic device;
   a selected one of said front panel or said back panel including a cavity including a floor and sidewalls extending there around formed in a surface thereof of a selected depth in a selected shape forming at least one panel cavity;
   said panel cavity including holding means comprising at least one projection extending upward normal to said floor of said panel cavity a selected distance less than said selected depth;
   a removable scented element disposed within said panel cavity, said scented element including a polymer impregnated with a fragrance;
   a cover including means for removable attachment to said panel cavity; and
   means for passive evaporation of aromatic volatiles to deliver the aroma selected from the group consisting of at least one pore, at least one aperture, at least one slits, and combinations thereof which enhance the evaporation of the aromatic volatile contained in said aromatic insert for allowing a fragrance impregnated within said polymer to evaporate into the air for the purpose of improving the perceived aroma in close proximity to a user.

2. A fragrance dispenser case for a hand held portable electronic device consisting of:
   a protective case having a front panel connecting to a back panel by opposing corresponding connecting side edges in parallel with one another in a spaced apart relationship for removably covering a portable electronic device;
   a selected one of said front panel or said back panel including a cavity including a floor and sidewalls extending there around formed in a surface thereof of a selected depth in a selected shape forming at least one panel cavity;
   a removable scented element disposed within said panel cavity;
   a cover including means for removable attachment to said panel cavity; and
   means for passive evaporation of aromatic volatiles from said scented element to evaporate into the air for the purpose of improving the perceived aroma in close proximity to a user.

3. A fragrance dispenser case for a portable electronic device comprising:
   a protective case having a front panel connecting to a back panel by opposing corresponding connecting side edges in parallel with one another in a spaced apart relationship for removably covering a portable electronic device;
   a selected one of said front panel or said back panel including a cavity including a floor and sidewalls extending there around formed in a surface thereof of a selected depth in a selected shape forming at least one panel cavity;
   said panel cavity including holding means comprising at least one projection extending upward normal to said floor of said panel cavity a selected distance less than said selected depth;
   a removable scented element disposed within said panel cavity, said scented element including a polymer impregnated with a fragrance;
   a cover including means for removable attachment to said panel cavity; and means for passive evaporation of aromatic volatiles to deliver the aroma selected from the group consisting of at least one pore, at least one aperture, at least one slits, and combinations thereof which enhance the evaporation of the aromatic volatile contained in said aromatic insert for allowing a fragrance impregnated within said polymer to evaporate into the air for the purpose of improving the perceived aroma in close proximity to a user.

4. The fragrance dispenser case for a portable electronic device of claim 3, wherein said scented element includes apertures therein and said holding means comprises a plurality of projections of corresponding size and shape to protrude through at least a portion of said apertures to hold said scented element in position within said cavity.

5. The fragrance dispenser case for a portable electronic device of claim 3, wherein said scented element comprises a copolymer ethylene vinyl acetate.

6. The fragrance dispenser case for a portable electronic device of claim 3, wherein said scented element comprises at least one bead, at least one pellet, at least one disc, at least one pill, at least one film, at least one button, and combinations thereof.

7. The fragrance dispenser case for a portable electronic device of claim 3, wherein said scented element comprises a molded shape.

8. The fragrance dispenser case for a portable electronic device of claim 3, wherein said scented element comprises a fragrance impregnated wax providing a scent releasing substrate.

9. The fragrance dispenser case for a portable electronic device of claim 3, wherein said scented element comprises from 0.5% to 99.5% by weight of a suitable substrate and from 0.5% to 90% by weight of a fragrance oil.

10. The fragrance dispenser case for a portable electronic device of claim 3, wherein said scented element is a blend with a polyethylene, a polypropylene, an ABS resin, a rubber, an elastomer, and combinations thereof.

11. The fragrance dispenser case for a portable electronic device of claim 3, wherein said panel cavity is shaped in the form of a clover leaf.

12. The fragrance dispenser case for a portable electronic device of claim 3, wherein said scented element is contained within a peelable film.

13. The fragrance dispenser case for a portable electronic device of claim 3, wherein said portable electronic device is selected from the group consisting of a cellular telephone, a tablet, an IPOD, a MP3 players, and a laptop.

14. The fragrance dispenser case for a portable electronic device of claim 3, wherein said portable electronic device comprises a communication device.

15. The fragrance dispenser case for a portable electronic device of claim 3, wherein said cover fits flush with a top surface of said front panel or said back panel.

16. The fragrance dispenser case for a portable electronic device of claim 3, wherein said portable electronic device is a hand held device.

* * * * *